US007166760B1

(12) United States Patent
Talbot

(10) Patent No.: US 7,166,760 B1
(45) Date of Patent: Jan. 23, 2007

(54) ANKLE BRACE

(76) Inventor: Meldon L. Talbot, 4671 Devonshire St., Boulder, CO (US) 80301

( * ) Notice: Subject to any disclaimer, the term of this patent is extended or adjusted under 35 U.S.C. 154(b) by 1056 days.

(21) Appl. No.: 09/706,992

(22) Filed: Nov. 6, 2000

Related U.S. Application Data

(63) Continuation-in-part of application No. 08/878,181, filed on Jun. 18, 1997, now abandoned.

(51) Int. Cl.
*A61F 13/00* (2006.01)

(52) U.S. Cl. .............................. 602/41; 602/5; 602/23; 602/27; 602/62; 602/65

(58) Field of Classification Search .................... 602/5, 602/23, 27–29, 61, 62, 65, 66, 16, 33; 128/882, 128/889, 892–894
See application file for complete search history.

(56) References Cited

U.S. PATENT DOCUMENTS 3,777,751 A * 12/1973 Wise .......................... 128/166
4,085,746 A * 4/1978 Castiglia ..................... 128/166
4,495,942 A * 1/1985 Palumbo ...................... 128/80
4,597,395 A * 7/1986 Barlow et al. ................ 128/80
4,753,228 A * 6/1988 Selner et al. ................. 128/80
5,090,404 A * 2/1992 Kallassy ...................... 602/65
5,676,641 A * 10/1997 Arensdorf et al. ............ 602/27
5,718,673 A * 2/1998 Shipstead .................... 602/27

* cited by examiner

*Primary Examiner*—Lalita M. Hamilton
(74) *Attorney, Agent, or Firm*—Shlesinger, Arkwright & Garvey LLP

(57) ABSTRACT

An ankle brace includes a single strap made of a substantially inelastic and flexible, non-adhesive material of sufficient length to be wrapped in a figure-eight configuration at least once about the ankle and foot, with one loop of the figure-eight passing around the back of the ankle, one loop passing under the foot in front of the heel, and the strap crossing above the foot. Hook and look fasteners secure one free end of the strap to the other end portion thereof to maintain tension in the strap and to retain the brace on the foot and ankle. The ankle brace can be worn under or over a stocking with equal support.

12 Claims, 1 Drawing Sheet

20

10

ANKLE BRACE

This application is a continuation-in-part of U.S. application Ser. No. 08/878,181 filed Jun. 18, 1997 now abandoned.

BACKGROUND OF THE INVENTION

This invention relates to the art of orthopedics, and more particularly to an ankle brace.

Prior inventors have developed a number of braces in the form of straps or webs intended to be wound about the ankle in one way or another. The free end or ends of the material are often secured by fasteners such as "Velcro" (generically: hook and loop fasteners) so that the brace remains tight and secure about the ankle.

In U.S. Pat. No. 4,085,746, Castiglia described an ankle wrap in the form of an elongated panel having Velcro-type fasteners along its length. The panel was made of an elastic material, specifically intended to brace the ankle joint without restricting walking and running movements.

Baker, in his U.S. Pat. No. 3,506,000, disclosed an ankle support having an inelastic body which lay behind the heel, but the body was secured to the foot by distinct elastic straps which were interconnected after they had been wrapped around the foot.

The Wise U.S. Pat. No. 3,777,751, has a substantially inelastic, flexible strap with Velcro fasteners and a "tongue". The strap loops around the ankle but the tongue must be secured to the lower leg, above the ankle, with adhesive tape or a "fastened gauntlet or collar". This brace is not a figure-eight type and requires some type of auxiliary attachment to the lower leg, either adhesive tape or a second gauntlet or collar.

An ankle support having non-stretch fabric components is shown in U.S. Pat. No. 5,090,404, but the construction is complex, including a foam under liner and numerous parts requiring assembly by sewing. U.S. Pat. No. 3,490,450 discloses a brace made of canvas, and U.S. Pat. No. 4,753,228, includes components of "limited elasticity". Neither, however, is a figure-eight type brace.

Prior wrapped braces of the figure-eight type are uniformly elastic, probably on the theory that elasticity is necessary to permit movement of the ankle, and for comfort. I have found, however, that better support is provided by such an ankle brace made of a substantially inelastic material, and that one can achieve acceptable levels of comfort with an inelastic yet flexible web wrapped in a figure-eight configuration about the foot and ankle. This ankle brace can be worn directly on the foot and ankle, or over a normal stocking for more comfort and equal support

SUMMARY OF THE INVENTION

An object of the invention is to provide a flexible but inelastic brace for supporting the ankle.

Another object of the invention is to provide an effective ankle brace that is comfortable enough to wear all day, every day, for people with unstable ankles as well as during participation in sports or other physically demanding activities.

Another object of the invention is to simplify the manufacture and application of an orthopedic ankle brace.

These and other objects are attained by an ankle brace formed of a single strap made of a substantially inelastic non-adhesive material of sufficient length to be wrapped at least once in a figure-eight configuration about the ankle and foot. One loop of the figure-eight passes around the back of the ankle, one loop passes under the foot in front of the heel, and the strap crosses above the foot. The strap has fasteners, preferable "Velcro", for securing the free end of the strap to the wrapped portion to maintain tension in the strap and to retain the brace on the foot and ankle. The ankle brace is equally effective whether worn inside or outside of a normal stocking.

BRIEF DESCRIPTION OF THE DRAWINGS

In the accompanying drawings.

BRIEF DESCRIPTION OF THE PREFERRED EMBODIMENT

Figure 1:
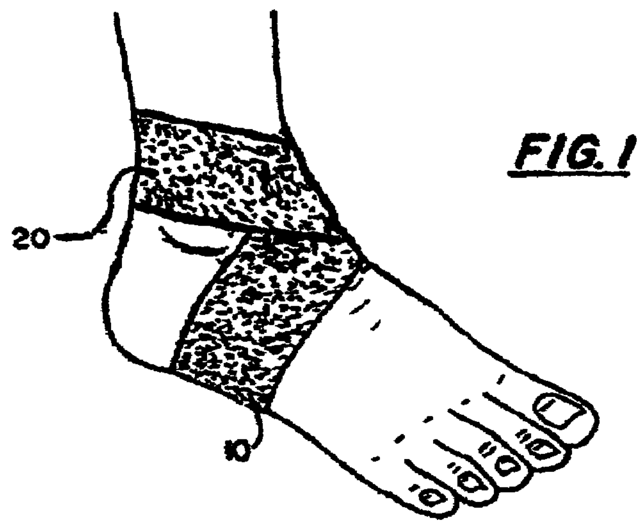
FIG. 1 is a perspective view, from above of an ankle brace embodying the invention, applied to a patient.
Figure 2:
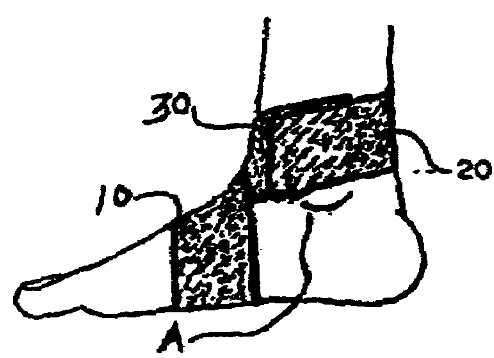
FIG. 2 is a side elevation thereof showing the preferred location of the hook and loop fasteners on a fully wrapped foot and ankle.
Figure 3:
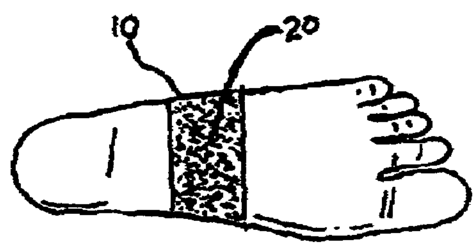
FIG. 3 is a bottom plan view thereof.

An ankle brace embodying the invention is shown in FIGS. 1–5. It comprises a single strap 10 made of a substantially inelastic yet flexible material, preferably of non-adhesive, constant-width web of a strong fabric. The fabric may be woven of a strong natural fiber such as cotton or linen, or a synthetic material such as nylon. The choice of material and choosing the dimensions of the strap for wrapping a foot of a particular size are matters of ordinary skill. This strap must by long enough to be wound in a figure-eight configuration completely about the ankle and foot, as shown in FIGS. 1–3, preferable at least once, and possibly more than once. Tension is maintained on the strap as it is wrapped; the tension is held until the free end of the strap has been secured to the outer surface of the strap. While hardware fasteners may be suitable, a hook and loop fastener is preferred because of its reliability, strength, great degree of adjustability, flexibility and comfort.

Figure 4:
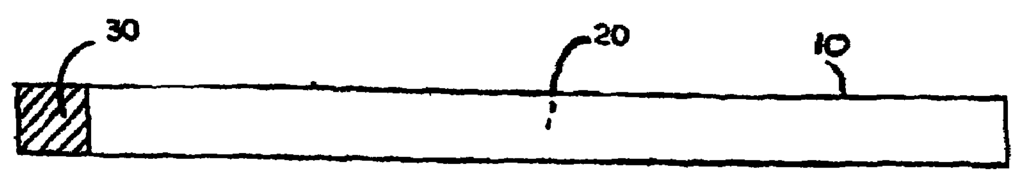
FIG. 4 is a plan view of one side of the brace, laid out flat, showing the preferred location of the array of hooks.
Figure 5:
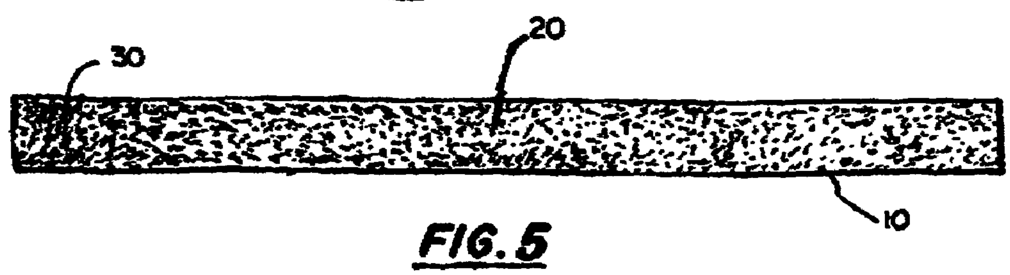
FIG. 5 is a plan view of the opposite side of the brace, laid out flat, showing the preferred location of the array of loops.

A hook and loop fastener comprises two complementary parts: one part with an array of plastic loops and another part with an array of plastic hooks for engaging the loops. In this invention, one of those parts is disposed on a free end of the web, and its counterpart is placed elsewhere of the web in a position permitting the parts to be pressed together when the strap has been wrapped about the foot and ankle. For example, as shown in FIGS. 4–5, the loop portion 20 may be on one side of the strap, in a position which will correspond to the outside of the brace, see FIG. 5. The loop portion 20 preferably covers all of the outside of the brace but may cover any portion of the outside of the brace on the condition that at least 1–5 inches of the end opposite and side opposite of the hook portion 30 of the brace is covered with loops. The hook portion 30 on the opposite side of the loops preferably covers 1–5 inches of one end of the strap, see FIG. 4, but may cover any portion of the strap on the condition that the hooks 30 are on the side opposite and end opposite of the loops 20. When the brace is wrapped about the foot and ankle in FIG. 2 the loop portion 20 is on the outside of the brace, near the inside ankle bone "A" of the foot. In this example, a patch of hook material 30 is sewn or otherwise applied to the one free end of the strap, on the inner surface, so that it can be pressed down against the loop-bearing end to hold the brace in place.

Alternatively, the entire length of the strap may be provided with hooks or loops on the first side, to simplify manufacture and installation. This could be achieved by attaching a full-length fastener part to one side of the strap, or by making the strap from a unitary stock material already having loops or hooks formed over one entire surface. The entire opposite side may be formed with hooks if loops were used on the first side or loops if hooks were used on the first side, if that does not prove uncomfortable; otherwise, small hook-bearing patches can be sewn to at least one of the ends of the strap on the side opposite from the loops, see FIGS. 4–5.

In use, the strap is wrapped preferably at least once, possible more than once, about the ankle and foot in a figure-eight configuration. Said figure-eight begins at the inside of the ankle, crosses over the medial arch, loops below the foot in front of the heel, crosses over itself above the medial arch, and loops around the back of the ankle and fastens to itself at said beginning end of said figure eight configuration at the inside of the ankle. The strap is maintained in tension while the ankle is wrapped; when the desired number of turns have been taken, the fastener patch 30 on the free end of the strap is pressed against the loops 20 on the outside of the wrapping to secure the brace. For additional comfort, the ankle brace can be worn over a normal stocking with equal support.

Since the invention is subject to modifications and variations, it is intended that the foregoing description and the accompanying drawings shall be interpreted as only illustrative of the invention defined by the following claims.

I claim:

1. A single strap ankle brace comprising a strap having a first and a second end, wherein said single strap ankle brace is made of a flexible substantially inelastic web of fabric, an array of plastic hooks disposed at only one of said first and second ends of said strap, an array of plastic loops for engaging said array of plastic hooks, said array of plastic loops being spaced on a surface of said strap, wherein said array of plastic hooks is separated and spaced apart on said strap from said array of plastic loops such that said array of plastic hooks and array of plastic loops may be pressed together when said strap is wrapped about the ankle and foot in a figure eight configuration which exposes said array of plastic loops, and wherein said figure eight configuration comprises a beginning end positioned at the inside of the ankle, crosses over the medial arch, loops below the foot in front of the heel, crosses over itself above the medial arch, and loops around the back of the ankle and fastens to itself at said beginning end of said figure eight configuration at the inside of the ankle.

2. The single strap ankle brace of claim 1 wherein said array of plastic hooks and said array of plastic loops are disposed on opposite sides of said strap.

3. The single strap ankle brace of claim 1 made of constant width fabric.

4. The single strap ankle brace of claim 1 made of non-adhesive material.

5. A method for bracing an ankle and associated foot which comprises:

(i) providing the single strap ankle brace of claim 1;

(ii) wrapping said single strap ankle brace around the ankle and associated foot in a figure eight configuration, wherein said wrapping comprises:

(a) positioning said end of said strap on which no array of plastic hooks is disposed;

(b) then passing a length of said strap at least once around the foot passing under the foot in front of the heel to provide one loop of said figure eight configuration then passing across a section of said strap above the foot and then around the back of the ankle to provide the other loop of said figure eight configuration, wherein said wrapping exposes said array of plastic loops, and wherein said wrapping provides a free end of said strap upon which an array of plastic hooks is disposed; and (iii) pressing said array of plastic loops exposed by said wrapping together with said array of plastic hooks on said free end of said strap.

6. A method for bracing an ankle and associated foot which comprises:

(i) providing the single strap ankle brace of claim 1;

(ii) wrapping said single strap ankle brace around the ankle and associated foot in a figure eight configuration, wherein said figure eight configuration comprises a beginning end positioned at the inside of the ankle, crosses over the medial arch, loops below the foot in front of the heel, crosses over itself above the medial arch, and loops around the back of the ankle and fastens to itself at said beginning end of said figure eight configuration at the inside of the ankle.

7. A single strap ankle brace comprising a strap having a first and a second end, wherein said single strap ankle brace is made of a flexible substantially inelastic web of fabric, an array of plastic hooks disposed at only said first end of said strap, an array of plastic loops for engaging said array of plastic hooks, said array of plastic loops being spaced on a surface of said strap, wherein said array of plastic hooks is separated and spaced apart on said strap from said array of plastic loops such that said array of plastic hooks and array of plastic loops may be pressed together when said strap is wrapped about the ankle and foot in a figure eight configuration which exposes said array of plastic loops, and wherein said figure eight configuration begins at the inside of the ankle, crosses over the medial arch, loops below the foot in front of the heel, crosses over itself above the medial arch, and loops around the back of the ankle and fastens to itself at said beginning end of said figure eight configuration at the inside of the ankle.

8. The single strap ankle brace of claim 7 wherein said array of plastic hooks and said array of plastic loops are disposed on opposite sides of said strap.

9. The single strap ankle brace of claim 7 made of constant width fabric.

10. The single strap ankle brace of claim 7 made of non-adhesive material.

11. A method for bracing an ankle and associated foot which comprises:

(i) providing the single strap ankle brace of claim 7;

(ii) wrapping said single strap ankle brace around the ankle and associated foot in a figure eight configuration;

wherein said wrapping comprises:

(a) positioning on the inside of the ankle said end of said strap on which no array of plastic hooks is disposed;

(b) then passing a length of said strap at least once around the foot passing under the foot in front of the heel to provide one loop of said figure eight configuration then passing across a section of said strap above the foot and then around the back of the ankle to provide the other loop of said figure eight configuration, wherein said wrapping exposes said array of plastic loops, and wherein said wrapping provides a free end of said strap upon which an array of plastic hooks is disposed; and (iii) pressing said array of plastic loops exposed by said wrapping together with said array of plastic hooks on said free end of said strap.

12. A method for bracing an ankle and associated foot which comprises:

(i) providing the single strap ankle brace of claim 7;

(ii) wrapping said single strap ankle brace at least once around the ankle and associated foot in a figure eight configuration, wherein said figure eight configuration comprises a beginning end positioned at the inside of the ankle, crosses over the medial arch, loops below the foot in front of the heel, crosses over itself above the medial arch, and loops around the back of the ankle and fastens to itself at said beginning end of said figure eight configuration at the inside of the ankle.

* * * * *